(12) United States Patent
Fialka et al.

(10) Patent No.: US 10,393,567 B2
(45) Date of Patent: Aug. 27, 2019

(54) CONTAINER SYSTEM FOR A FLUID AND METHOD FOR PRODUCING SAME

(71) Applicant: CONTINENTAL AUTOMOTIVE GMBH, Hannover (DE)

(72) Inventors: Otakar Fialka, Frydek-Mistek (CZ); Karl-Friedrich Pfeiffer, Erlangen (DE)

(73) Assignee: Continental Automotive GmbH, Hannover (DE)

( * ) Notice: Subject to any disclaimer, the term of this patent is extended or adjusted under 35 U.S.C. 154(b) by 208 days.

(21) Appl. No.: 15/585,208

(22) Filed: May 3, 2017

(65) Prior Publication Data

US 2017/0234718 A1 Aug. 17, 2017

Related U.S. Application Data

(63) Continuation of application No. PCT/EP2015/076180, filed on Nov. 10, 2015.

(30) Foreign Application Priority Data

Nov. 11, 2014 (DE) .................. 10 2014 223 007

(51) Int. Cl.
*G01N 29/28* (2006.01)
*G01F 23/296* (2006.01)
*G01M 13/04* (2019.01)

(52) U.S. Cl.
CPC .......... *G01F 23/296* (2013.01); *G01N 29/28* (2013.01); *G01M 13/04* (2013.01)

(58) Field of Classification Search
CPC ....... G01F 23/296; G01N 29/28; G01M 13/04
(Continued)

(56) References Cited

U.S. PATENT DOCUMENTS 4,487,065 A * 12/1984 Carlin .................. G01F 23/296
340/870.16
4,597,294 A * 7/1986 Brill, III ............... F22B 37/003
376/252
(Continued)

FOREIGN PATENT DOCUMENTS

CN 103097867 A 5/2013
DE 102010035008 A1 2/2012
(Continued)

OTHER PUBLICATIONS

International Search Report and Written Opinion dated Feb. 22, 2016 from corresponding International Patent Application No. PCT/EP2015/076180.
(Continued)

*Primary Examiner* — Jacques M Saint Surin

(57) ABSTRACT

A container system, having a container with an outer wall and a cavity which has either a slotted-guide element or a sliding block, a sound transducer unit with a longitudinal axis, which includes the other of the sliding block or the slotted-guide element, and a coupling element for acoustically coupling the sound transducer unit with the container. A contour of the slotted-guide element is formed such that, when introducing the sound transducer unit into the cavity, a first path of movement of the sound transducer unit relative to the container occurs, without mechanical contact of the coupling element with either the sound transducer unit or the outer wall. A second path of movement occurs, where the sound transducer unit pivots relative to the container until the sound transducer unit reaches an end position, where the coupling element is pressed in between the outer wall and the sound transducer unit.

21 Claims, 14 Drawing Sheets

(58) Field of Classification Search
USPC ............................................................ 73/593
See application file for complete search history.

(56) References Cited

U.S. PATENT DOCUMENTS

| | | | |
|---|---|---|---|
| 4,770,038 A | | 9/1988 | Zuckerwar et al. |
| 5,576,492 A | * | 11/1996 | Phalin .................. G01N 29/225 |
| | | | 73/618 |
| 5,586,085 A | | 12/1996 | Lichte |
| 5,942,687 A | * | 8/1999 | Simmonds ............. G01B 17/02 |
| | | | 73/579 |
| 6,289,728 B1 | * | 9/2001 | Wilkins .................. G01F 23/62 |
| | | | 73/149 |
| 2002/0078751 A1 | * | 6/2002 | Ziola ...................... G01B 17/02 |
| | | | 73/598 |
| 2005/0284217 A1 | | 12/2005 | Miyagawa et al. |
| 2008/0011060 A1 | * | 1/2008 | Lynnworth .......... G01N 29/024 |
| | | | 73/64.53 |
| 2013/0074601 A1 | | 3/2013 | Jackson |

FOREIGN PATENT DOCUMENTS

| | | |
|---|---|---|
| EP | 0769682 A2 | 4/1997 |
| JP | 2007139437 A | 6/2007 |

OTHER PUBLICATIONS

German Office Action dated Sep. 14, 2015 for corresponding German Application No. 10 2014 223 007.1.

\* cited by examiner

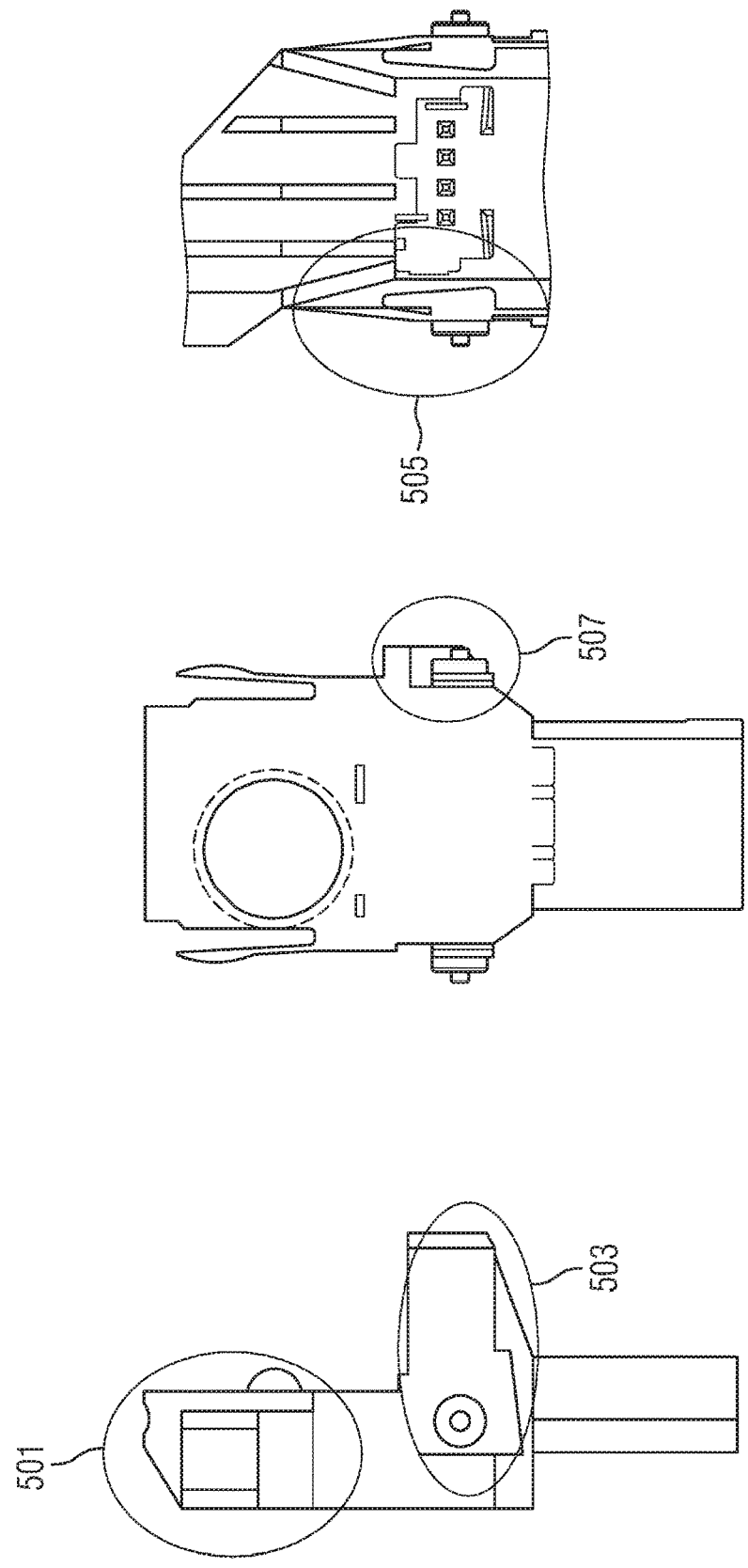

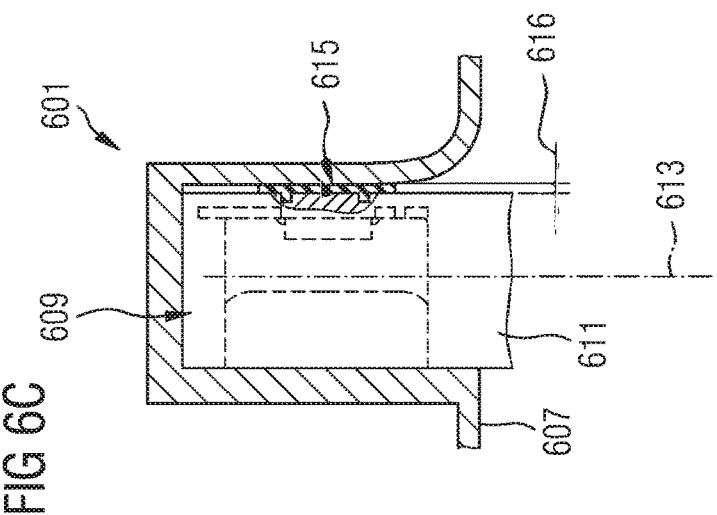
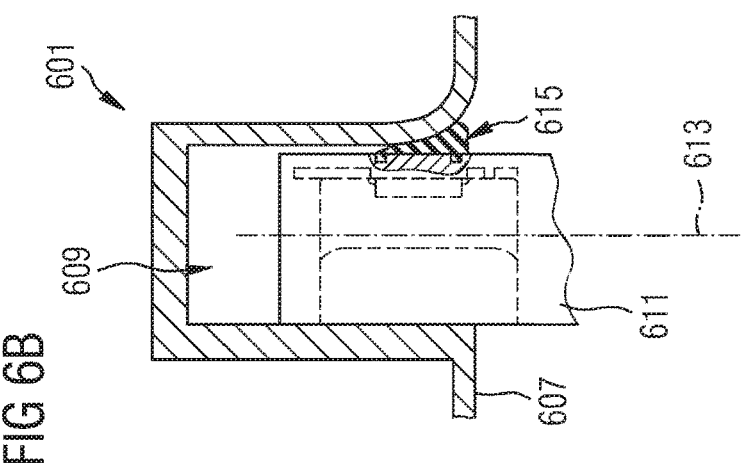
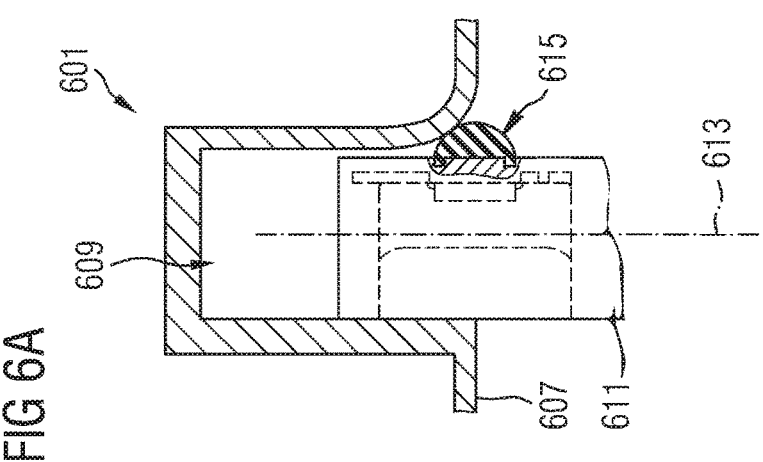

CONTAINER SYSTEM FOR A FLUID AND METHOD FOR PRODUCING SAME

CROSS-REFERENCE TO RELATED APPLICATIONS

This application claims the benefit of PCT Application PCT/EP2015/076180, filed Nov. 10, 2015, which claims priority to German Application DE 10 2014 223 007.1, filed Nov. 11, 2014. The disclosures of the above applications are incorporated herein by reference.

FIELD OF THE INVENTION

The present invention concerns a container system for a fluid and a method for producing a container system for a fluid.

BACKGROUND OF THE INVENTION

To measure a fluid in a fluid container, in particular an acoustic measuring device may be used. A sound transducer of the acoustic measuring device may work both as a sound generator and as a sound receiver. To determine a height of a fluid surface or a concentration of the fluid in the fluid container, sound pulses may be emitted by the sound transducer into the fluid to be measured. The sound pulses may be reflected by an interface of the fluid to a further medium. Conclusions on properties of the fluid in the fluid container are drawn from the run time of the sound pulses.

SUMMARY OF THE INVENTION

The object on which the invention is based is to create a container system for a fluid which allows a precise and reliable measurement of the fluid. It is also an object of the invention to create a method for producing a container system for a fluid which allows a precise and reliable measurement of the fluid.

According to a first aspect, the invention is distinguished by a container system for a fluid which comprises a container for storing the fluid. The container has an outer wall and a cavity. Either a slotted-guide element or a sliding block is assigned to the container.

The container system furthermore comprises a sound transducer unit for measuring the fluid. The sound transducer unit has a longitudinal axis. The sliding block or the slotted-guide element respectively is assigned to the sound transducer unit.

Furthermore, the container system has a coupling element for acoustically coupling the sound transducer unit with the container. The slotted-guide element and the sliding block form a sliding block guide for guiding the sound transducer unit relative to the container. A contour of the slotted-guide element is formed such that, when the sound transducer unit is introduced into the cavity, a first movement travel of the sound transducer unit relative to the container takes place. The first movement travel is substantially free from a mechanical contact of the coupling element with either the sound transducer unit or the outer wall.

The contour of the slotted-guide element is furthermore configured such that thereafter, a second movement travel with a pivoting of the sound transducer unit relative to the container takes place until the sound transducer unit reaches an end position in which the coupling element is pressed between the outer wall and the sound transducer unit.

The coupling element allows compensation for production tolerances, which helps to avoid an air or moisture inclusion between the sound transducer unit and the outer wall of the container. This ensures a particularly efficient acoustic coupling of the sound transducer unit and the outer wall. The coupling element in this context contributes to a reliable and precise measurement of the fluid by the sound transducer unit.

Such a guidance of the movement of the sound transducer unit and container relative to each other makes it possible to avoid an undesirable deformation of the coupling element on production of the container system. Advantageously, a particularly reliable operation of the container system is thus possible. Furthermore, assembly of the container system is possible without additional components such as a wedge and screw.

In this context for example, the slotted-guide element is assigned to the container and the corresponding sliding block is assigned to the sound transducer unit. Alternatively for example, the slotted-guide element is assigned to the sound transducer unit and the corresponding sliding block is assigned to the container.

The slotted-guide element is for example configured as a slot, a web or a groove. The sliding block is for example configured as a pin or a peg. The sliding block is for example force-guided on both sides by the slotted-guide element. The path of the contour of the slotted-guide element predefines a transmission function of the sliding block guide formed by the sliding block and the slotted-guide element. Such guidance may also be called a sliding block guidance.

A force which acts on the coupling element on production of the container system, in the first movement travel of the sound transducer unit relative to the container, is substantially provoked by just one of the sound transducer unit and the outer wall, so that the coupling element experiences no undesirable deformation in the first movement travel. In particular, the force is provoked either only by the sound transducer unit or only by the outer wall.

In particular, the first movement travel of the sound transducer unit relative to the container takes place along the longitudinal axis. The coupling element is advantageously already arranged on the sound transducer unit.

Alternatively, the coupling element is already arranged on the outer wall.

The coupling element may also be designated as a coupling pad. The coupling pad is preferably made of a rubber-like material.

In an advantageous embodiment according to the first aspect, either a pivot head or a pivot cup is assigned to the container. Furthermore, the pivot cup or the pivot head respectively is assigned to the sound transducer unit. The pivot head and the pivot cup form an articulation joint for guiding the sound transducer unit relative to the container in the second movement travel.

The articulation joint allows a reliable and precise guidance of the movement of the sound transducer unit and container relative to each other, so that an undesirable deformation of the coupling element is avoided on production of the container system.

In a further advantageous embodiment according to the first aspect, the slotted-guide element and the sliding block are configured for fixing the sound transducer unit in the end position relative to the container.

This contributes to a durably reliable operation of the container system. Fixing the sound transducer unit relative to the container by means of the slotted-guide element and sliding block contributes to simple assembly of the container system.

In a further advantageous embodiment according to the first aspect, at least one additional guide wall is assigned to the container and comprises part of the sliding block guide.

In particular in the case of fixing of the sound transducer unit relative to the container by means of the slotted-guide element and sliding block, this allows the fixing to be configured accessible from the outside and hence easily releasable. Furthermore, a partial arrangement and/or fixing of the sound transducer unit outside the cavity minimizes any volume loss of the container due to the sound transducer unit.

For example, the outer wall comprises the at least one guide wall. Alternatively, the at least one guide wall is for example welded to the outer wall.

According to a second aspect, the invention is distinguished by a method for producing a container system for a fluid, which comprises a container for storing the fluid. The container has an outer wall and a cavity.

The container system furthermore comprises a sound transducer unit for measuring the fluid. The sound transducer unit has a longitudinal axis.

Furthermore, the container system comprises a coupling element for acoustically coupling the sound transducer unit with the container. The sound transducer unit is introduced into the cavity in a first movement travel relative to the container such that the coupling element is substantially free from mechanical contact with either the sound transducer unit or the outer wall.

Furthermore, in a second movement travel, the sound transducer unit is pivoted relative to the container until the sound transducer unit reaches an end position relative to the container in which the coupling element is pressed between the outer wall and the sound transducer unit.

Such a movement travel of the sound transducer unit and container relative to each other prevents an undesirable deformation of the coupling layer on production of the container system. Advantageously, this allows a particularly reliable operation of the container system.

The movement travel of the sound transducer unit and the container relative to each other may for example be guided mechanically. Alternatively and/or additionally, the container system in this context may for example comprise guide elements.

In a further advantageous embodiment according to the second aspect, either a slotted-guide element or a sliding block is assigned to the container.

Furthermore, the sliding block or the slotted-guide element respectively is assigned to the sound transducer unit. The slotted-guide element and the sliding block are coupled into a sliding block guide for guiding the sound transducer unit relative to the container in the first movement travel and in the second movement travel.

In a further advantageous embodiment according to the second aspect, on reaching the end position relative to the container, the sound transducer unit is fixed by the slotted-guide element and the sliding block.

In a further advantageous embodiment according to the second aspect, either a pivot head or a pivot cup is assigned to the container.

Furthermore, the pivot cup or the pivot head respectively is assigned to the sound transducer unit. The pivot head and the pivot cup are coupled into an articulation joint for guiding the sound transducer unit relative to the container in the second movement travel.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 5a-5i are various views of a second embodiment of a container system, according to embodiments of the present invention; and FIGS. 6a-6c are various sectional views of a portion of a container and a portion of a transducer unit during various steps in an assembly process of a second embodiment of a container system, according to embodiments of the present invention.

DETAILED DESCRIPTION OF THE PREFERRED EMBODIMENTS

Figure 1:
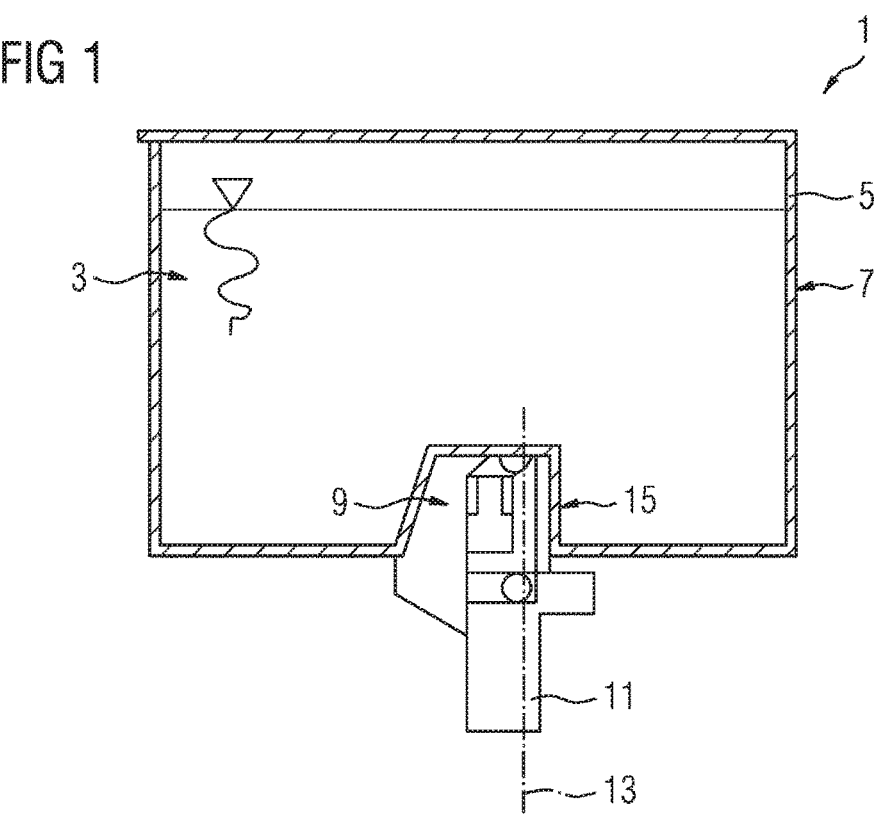
FIG. 1 is a partial sectional view of a container system, according to embodiments of the present invention.

The following description of the preferred embodiment(s) is merely exemplary in nature and is in no way intended to limit the invention, its application, or uses.

Elements of the same construction or function carry the same reference numerals across all figures.

FIG. 1 shows a container system 1 for a fluid 3 in mounted state, including a container 5 for storing the fluid 3. The container 5 has an outer wall 7 and a cavity 9.

The container system 1 furthermore comprises a sound transducer unit 11 for measuring the fluid 3. The sound transducer unit 11 is for example configured to emit an ultrasound signal into the container 5, and/or to receive a reflected ultrasound signal from the container 5. In this context, for example a concentration of the fluid 3 or a filling level of the fluid 3 in the container 5 is determined. The fluid 3 is for example a liquid medium for reduction of emissions in exhaust gases, which preferably comprises a reduction agent and/or a reduction agent precursor, for example a watery urea solution.

The cavity 9 of the container 5 is configured to receive the sound transducer unit 11. In mounted state, the sound transducer unit 11 protrudes for example at least partially into the cavity 9. In particular, the sound transducer unit 11 is configured such that a main radiation direction of the ultrasound signals runs parallel to a base portion of the container 5. In mounted state, the sound transducer unit 9 is in this context arranged for example with its longitudinal axis 13 perpendicular to a base portion of the container 5.

Furthermore, the container system 1 includes a coupling element 15 which is configured for acoustically coupling the sound transducer unit 11 with the container 5. The coupling element 15 is for this arranged in a coupling region of the outer wall 7. In particular, the coupling element 15 helps to avoid an air or moisture inclusion between the outer wall 7 and the sound transducer unit 11, and/or to compensate for production tolerances.

The coupling element 15 is made from an elastic material. In particular, the coupling element 15 is made from a rubber-like material, such as for example silicone.

In order to guarantee a reliable and precise measurement of the fluid 3, in particular it is necessary for the coupling element 15 to lie as evenly and tightly as possible against the outer wall 7 and the sound transducer unit 11. Advantageously, for this the coupling element 15 is pressed between the outer wall 7 and the sound transducer unit 11.

FIGS. 6a to 6c show assembly steps of a further container system 601 with a container 605 which has an outer wall 607 and a cavity 609. The further container system 601 also comprises a sound transducer unit 611 with a longitudinal axis 613 on which the coupling element 615 is arranged. When the sound transducer unit 611 is introduced into the cavity 609, the coupling element 615 is compressed due to a predefined distance 616 between the outer wall 607 and the sound transducer unit 611. An undesirable deformation of the coupling element 615 then results (see FIG. 6b).

Figure 2A:
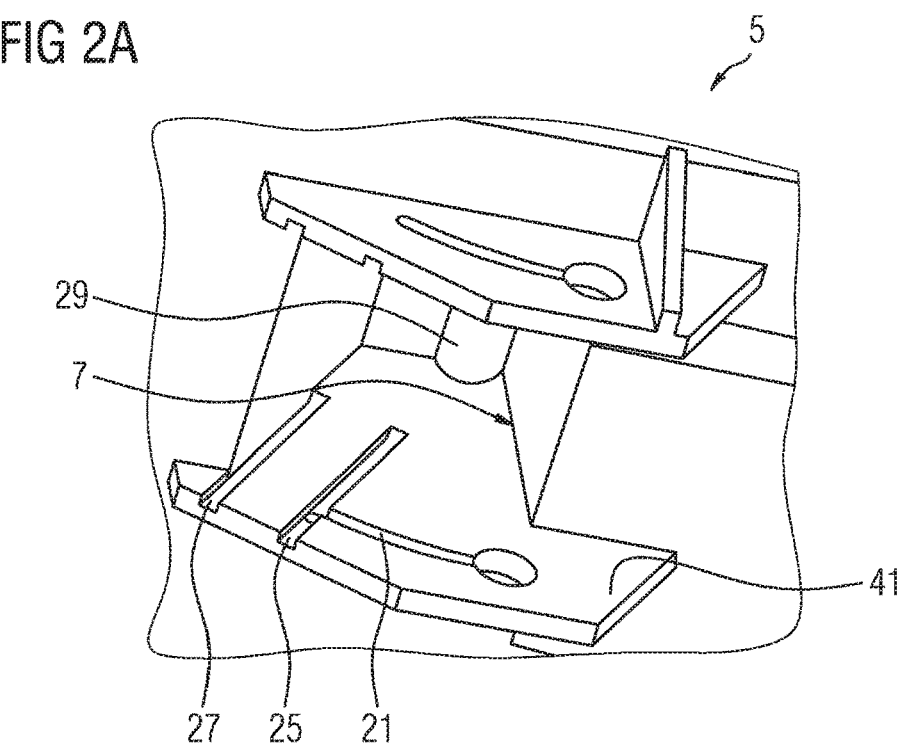
FIG. 2a is a perspective view of part of a container used as part of a container system, according to embodiments of the present invention.
Figure 2B:
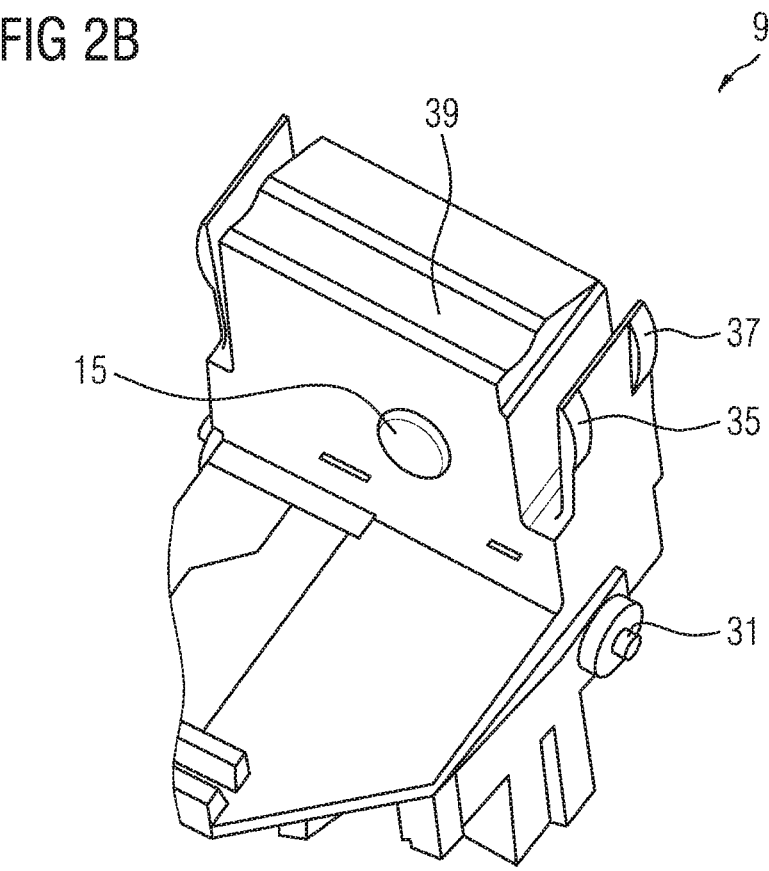
FIG. 2b is a perspective view of a sound transducer unit used as part of a container system, according to embodiments of the present invention.

In this context, slotted-guide elements 21, 25, 27 are assigned to the container 5 of the container system 1 according to FIG. 1 (see FIG. 2a). Furthermore, sliding blocks 31, 35, 37 are assigned to the sound transducer unit 11 of the container system 1 according to FIG. 1 (see FIG. 2b). In particular, further slotted-guide elements corresponding to the slotted-guide elements 21, 25, 27 are arranged on a side of the cavity opposite the slotted-guide elements 21, 25, 27, and further sliding blocks corresponding to the sliding blocks 31, 35, 37 are arranged on a side of the sound transducer unit 11 opposite the sliding blocks 31, 35, 37.

In another exemplary embodiment, the slotted-guide elements 21, 25, 27 are for example assigned to the sound transducer unit 11, and the sliding blocks 31, 35, 37 are assigned to the container 5.

The slotted-guide elements 21, 25, 27 are configured to be able to be coupled with the sliding blocks 31, 35, 37 to form a sliding block guide for guiding the sound transducer unit 11 relative to the container 5.

In addition and/or alternatively, a pivot head 29 for example is assigned to the container 5 (see FIG. 2a). Furthermore, a pivot cup 39 is assigned to the sound transducer unit 11 (see FIG. 2b). The pivot head 29 is for example a bulge of the outer wall 7.

In another exemplary embodiment, the pivot head 29 is for example assigned to the sound transducer unit 11, and the pivot cup 39 is assigned to the container 5.

The pivot head 29 is configured to be able to be coupled with the pivot cup 39 to form an articulation joint for guiding the sound transducer unit 11 relative to the container 5.

A contour of the slotted-guide elements 21, 25, 27 is configured such that on assembly of the container system 1, a first movement travel of the sound transducer unit 11 relative to the container 5 takes place in guided fashion such that the coupling element 15 is substantially free from mechanical contact with either the sound transducer unit 11 or the outer wall 7.

In particular in this context, substantially only a force either from the sound transducer unit 11 or from the outer wall 7 acts on the coupling element, so that the coupling element 15 does not undergo any undesirable deformation in the first movement travel.

For example, a volume of the cavity 9 is increased in particular in relation to a volume of the cavity 609 of the further container system 601. In particular, a side of the outer wall 7 opposite the coupling region of the outer wall 7 is chamfered in this context so that it encloses an angle with the coupling region of the outer wall 7. The sound transducer unit 11 is introduced in the first movement travel for example parallel to the side of the outer wall 7 opposite the coupling region. In particular, the first movement travel takes place along the longitudinal axis 13.

The contour of the slotted-guide elements 21, 25, 27 is furthermore configured such that on assembly, following the first movement travel, a second movement travel of the sound transducer unit 11 relative to the container 5 takes place in guided fashion with a pivoting of the sound transducer unit 11 relative to the container 5, until the sound transducer unit 11 reaches an end position relative to the container 5 in which the coupling element 15 is pressed between the outer wall 7 and the sound transducer unit 11.

Advantageously, this guarantees a controlled deformation of the coupling element 15. This has the advantage that the coupling element 15 lies for example particularly evenly between the sound transducer unit 11 and the outer wall 7. In particular, this allows a particularly reliable operation of the container system 1.

The slotted-guide elements 21, 25, 27 are in particular configured as a recess, for example as a slot, web or groove. The sliding blocks 31, 35, 37 are in particular configured correspondingly as a protrusion, for example as a guide pin, peg or rail. The sliding block guide formed by the slotted-guide elements 21, 25, 27 and the sliding blocks 31, 35, 37 may also be designated as a slot-and-peg joint or a tongue-and-groove joint, and configured couplably together for guiding the sound transducer unit 9 relative to the container 5.

Figure 3:
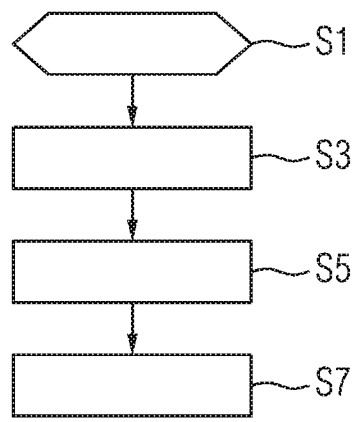
FIG. 3 is flow diagram for production of a container system, according to embodiments of the present invention.
Figure 4A:
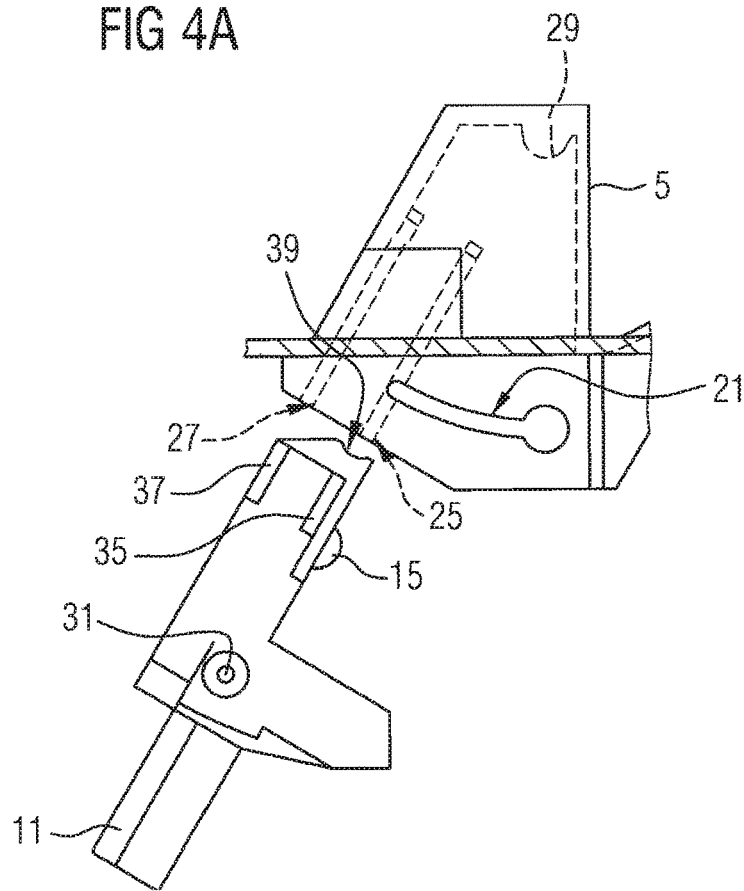
FIGS. 4a-4d are side views of a transducer unit and a portion of a container during various steps in an assembly process of a container system, according to embodiments of the present invention.
Figure 4B:
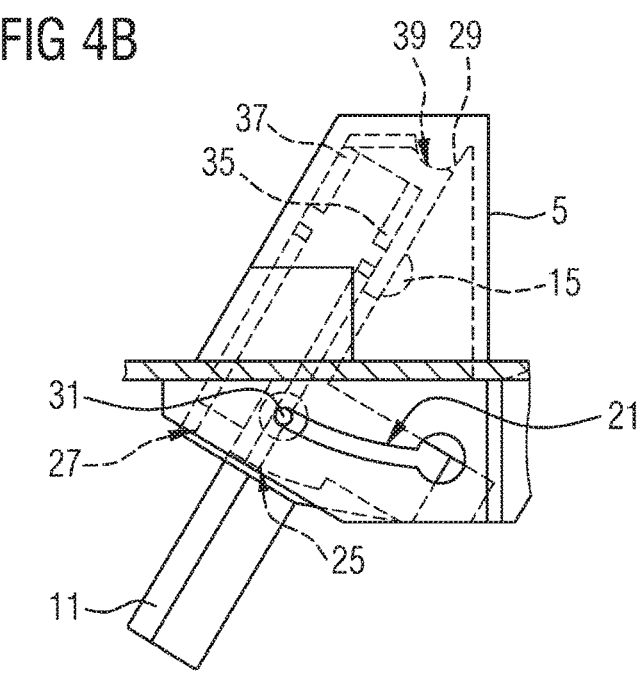
Figure 4C:
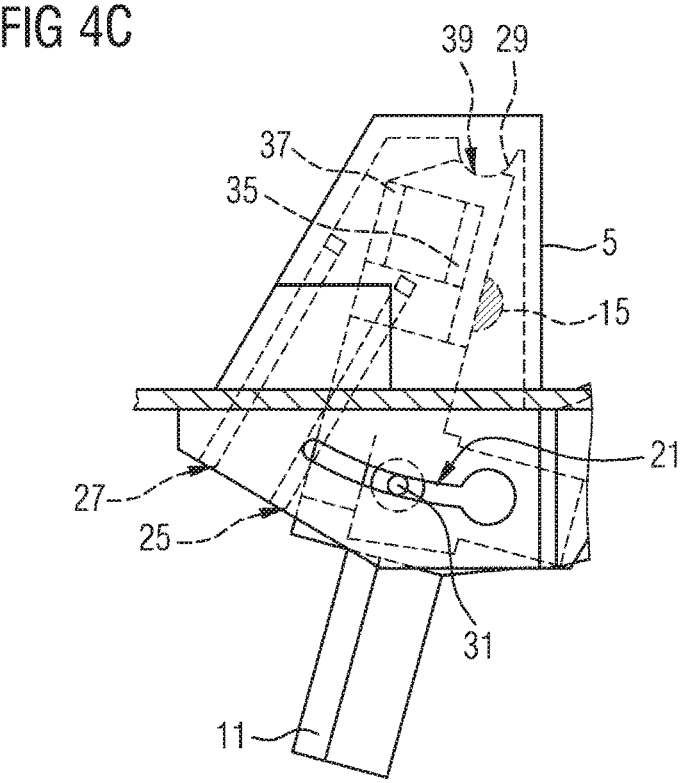
Figure 4D:
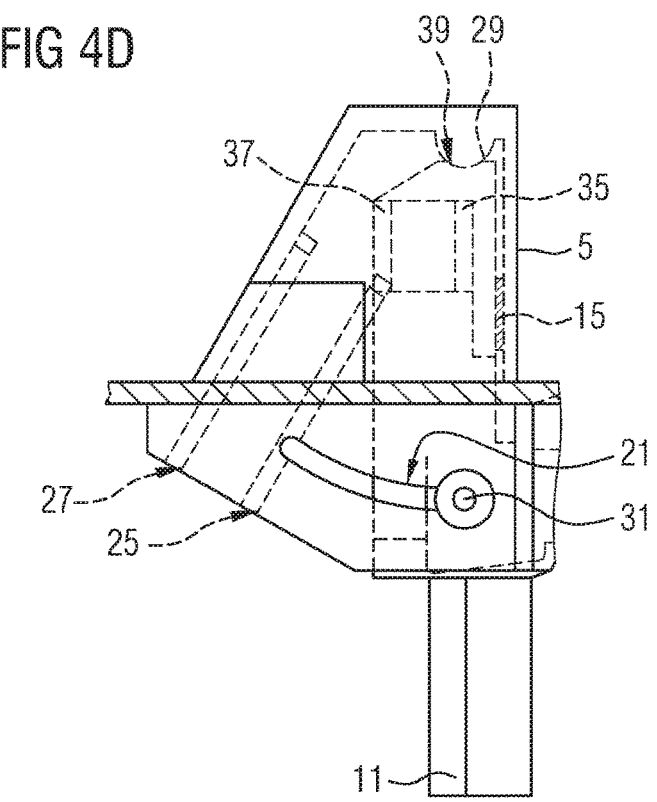

The assembly steps for production of the container system 1 are described below with reference to the flow diagram of FIG. 3, and to FIGS. 4a-4d.

In a step S1 (FIG. 4a), the container 5, the sound transducer unit 11 and the coupling element 15 are provided. The coupling element 15 is preferably attached to the sound transducer unit 11, for example by means of an adhesive joint, injection moulding or by interference. In other exemplary embodiments, the coupling element 15 is for example attached to the coupling region of the outer wall 7.

The sliding blocks 35, 37, configured as rails, are coupled to the slotted-guide elements 25, 27, configured as channels, and the sound transducer unit 11 is inserted guided thereby along the longitudinal axis 13 into the cavity 9. A width of the sliding blocks 35, 37 substantially corresponds to a width of the slotted-guide elements 25, 27. The sliding blocks 35, 39 and the slotted-guide element 25 are for example arranged on the longitudinal axis 13, so that in this first movement travel of the sound transducer unit 11 relative to the container 5, the sliding block 39, configured as a pin, is also coupled to the slotted-guide element 25 and thus contributes to an axial guidance. A first diameter of the sliding block 31 in this context substantially corresponds to the width of the slotted-guide element 25.

The sliding blocks 35, 37, configured as rails, and the slotted-guide elements 25, 27, configured as channels, are in particular parallel to each other to allow a particularly precise rectilinear guidance.

In a subsequent step S3 (FIG. 4b), the sound transducer unit 11 reaches an axial end position in which the pivot cup 39 is coupled to the pivot head 29. Furthermore, the sliding block 31 is coupled to the slotted-guide element 21. The sliding blocks 35, 37 are in particular configured elastic so that on reduced depth of the slotted-guide elements 25, 27, they are pressed away in the direction of the sound transducer unit 11. Advantageously, the sliding blocks 35, 37 are decoupled from the slotted-guide elements 25, 27 when the sound transducer unit 11 reaches the axial end position, so that a subsequent pivoting of the sound transducer unit 11 is possible in a step S5.

In a step S5 (FIG. 4c), in the second movement travel of the sound transducer unit 11 relative to the container 5, the sound transducer unit 11 is guided by the sliding block 31 in the slotted-guide element 21, and the articulation joint 29, 39 is pivoted about an axis of the articulation joint 29, 39.

Only in a subsequent step S7 (see also FIG. 4d) does the coupling element 15 come into mechanical contact with the outer wall 7, and is pressed between the sound transducer unit 11 and the outer wall 7. In the end position of the sound transducer unit 11 relative to the container 5, the sound transducer unit 11 is arranged with its longitudinal axis 13 in particular parallel to the coupling region of the outer wall 7.

The sound transducer unit 11 is fixed in the end position relative to the container 5 in particular for example by the sliding block 31 and the slotted-guide element 21. For example, the sliding block 31 for this has a second diameter, on a side facing towards the sound transducer unit 11, which is in particular greater than the first diameter of the sliding block 31 on a side facing away from the sound transducer unit 11.

The slotted-guide element 21 has a widening corresponding to the end position of the sound transducer unit 11 relative to the container 5, which substantially corresponds to the second diameter of the sliding block 31.

The sliding block 31 furthermore comprises a spring element which presses the sliding block 31 away from the sound transducer unit 11 in the direction of the slotted-guide element 21, so that the sliding block 31 engages with its second diameter in the widening when the sound transducer unit 11 reaches the end position relative to the container 5.

For example, in this context a guide wall 41 is assigned to the container 5 (see FIG. 2a), which comprises the slotted-guide element 21 so that this is accessible from the outside and the fixing may easily be released.

Figure 5B:
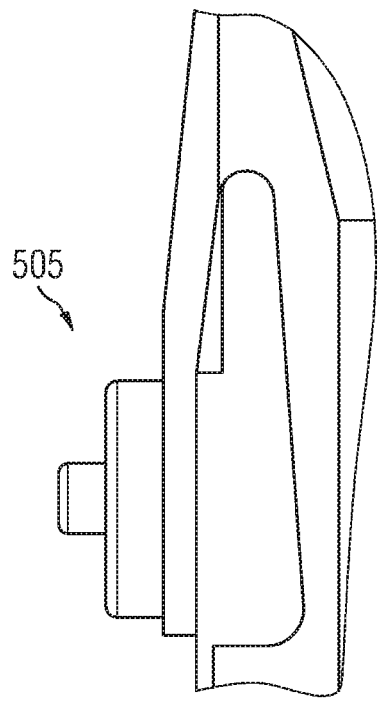
Figure 5B:
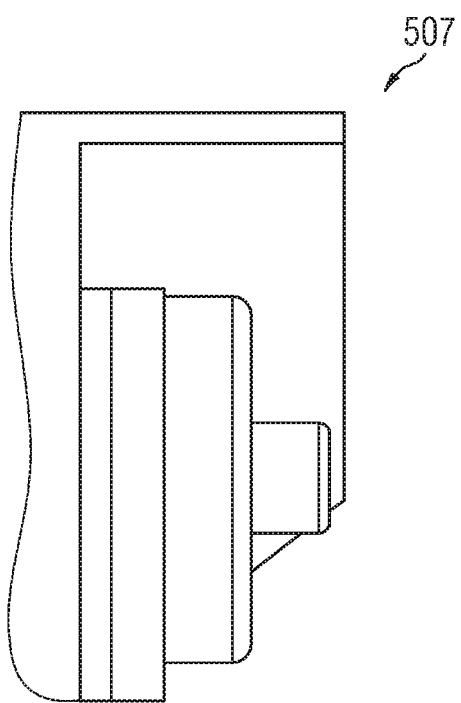

FIGS. 5a-5i depict components of a second container system. FIG. 5a shows a sound transducer unit from a side, front and top view, with a pair of vertical clips 501 for moving and blocking the sound transducer unit in an end position, and a pair of horizontal clips 503, 505, 507 for pivoting and fixing in the end position. FIG. 5b shows a detail view of the horizontal clips 505, 507 from a front and top view.

Figure 5C:
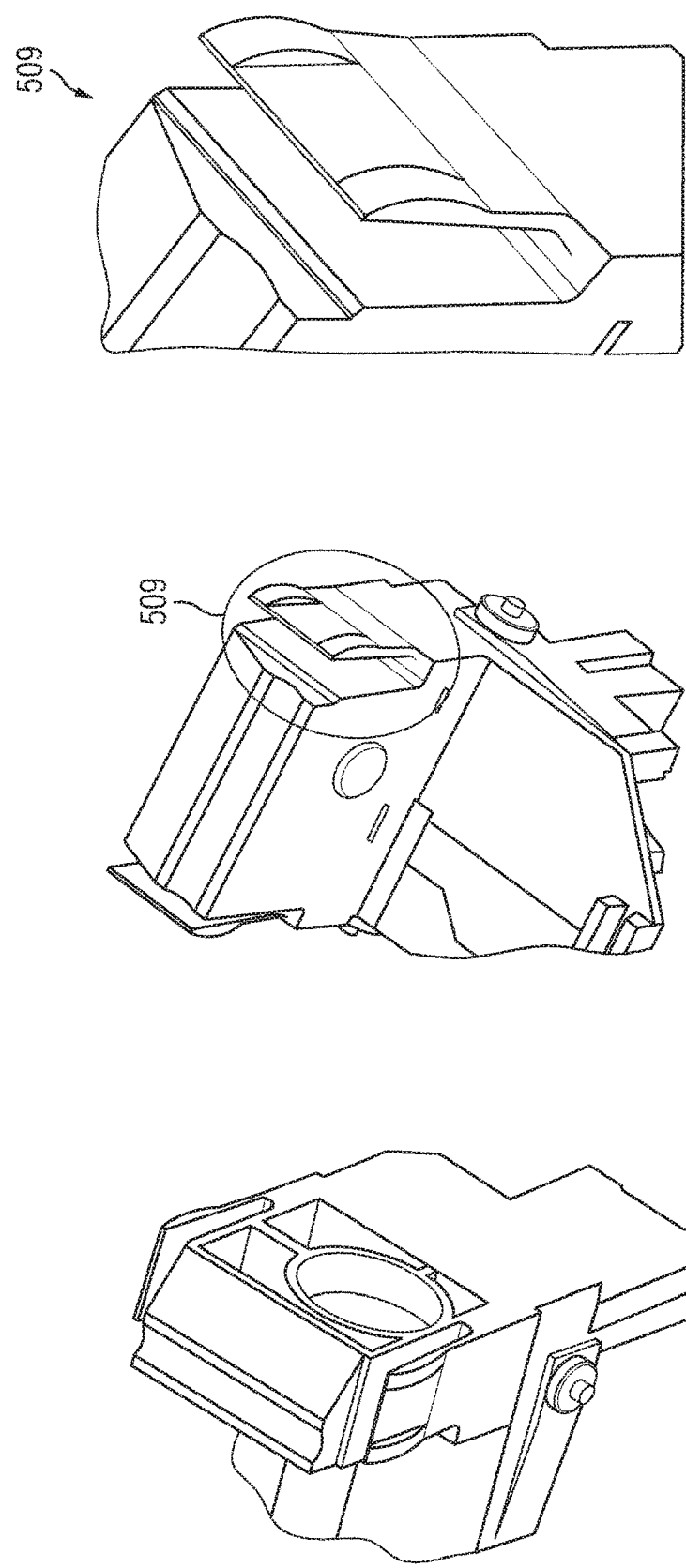

FIG. 5c shows further perspective depictions of the sound transducer unit and a detail view of the vertical clip 509.

Figure 5D:
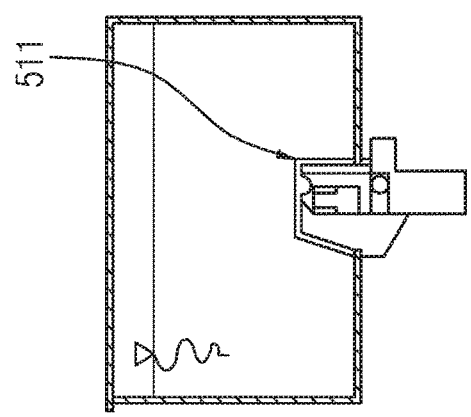
Figure 5D:
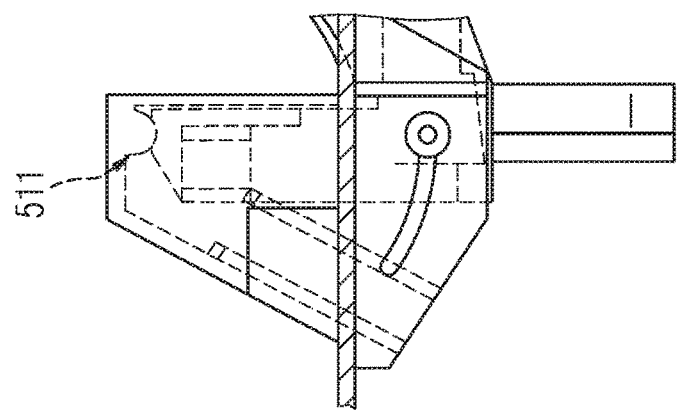
Figure 5D:
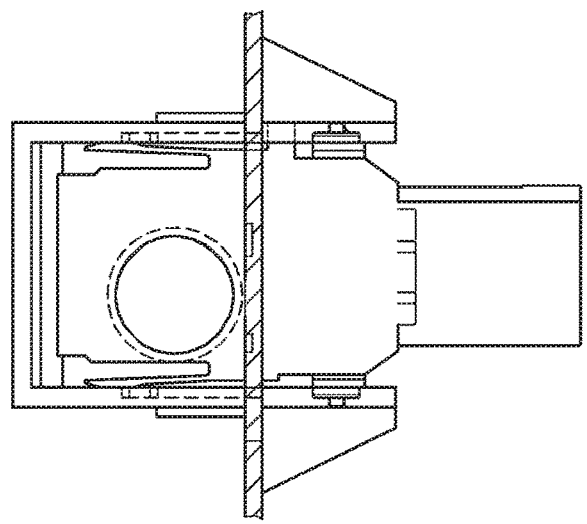

FIG. 5d shows the sound transducer unit and its position in the container in an overall view, and from a side and front perspective, with a bulge 511 of an outer wall of the container.

Figure 5E:
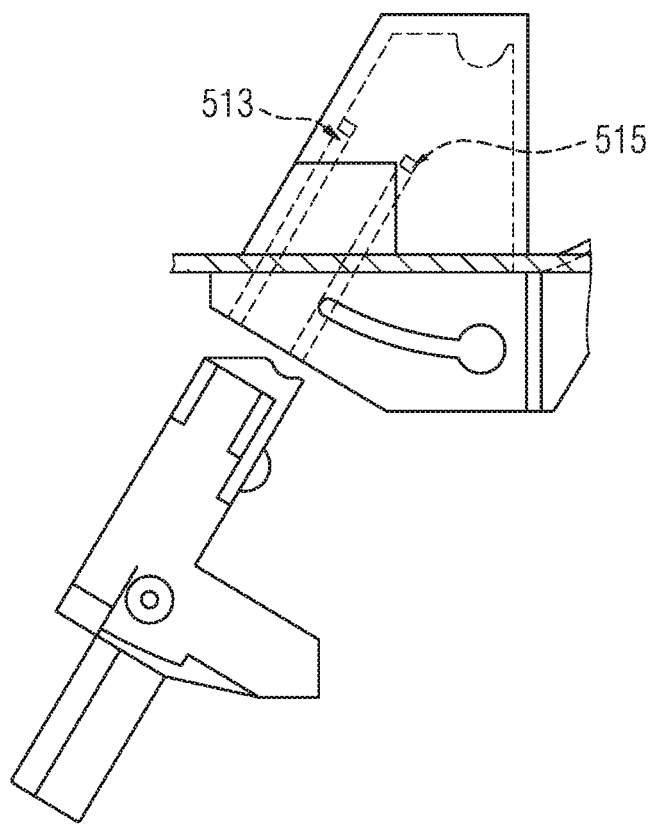
Figure 5E:
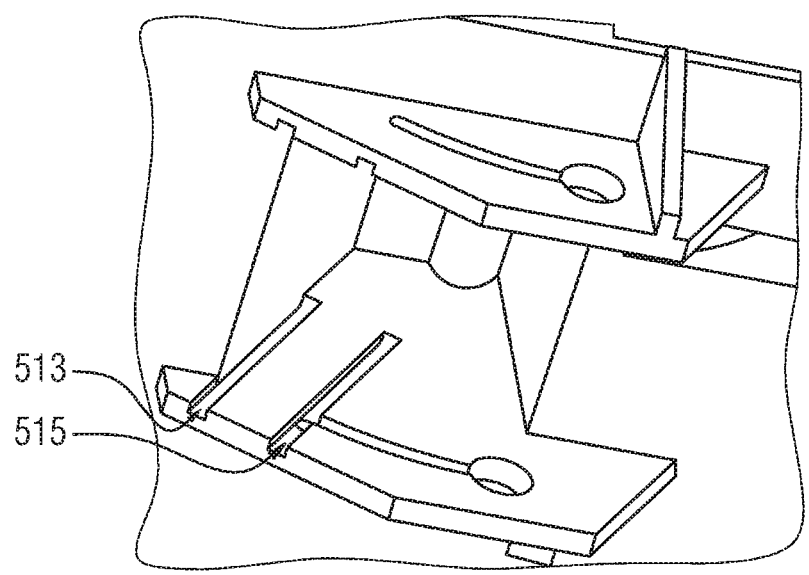

FIG. 5e shows a first position of the sound transducer unit during assembly of the second container system, in each case with two opposing parallel channels 513, 515 in the outer wall for movement of the sound transducer unit.

Figure 5F:
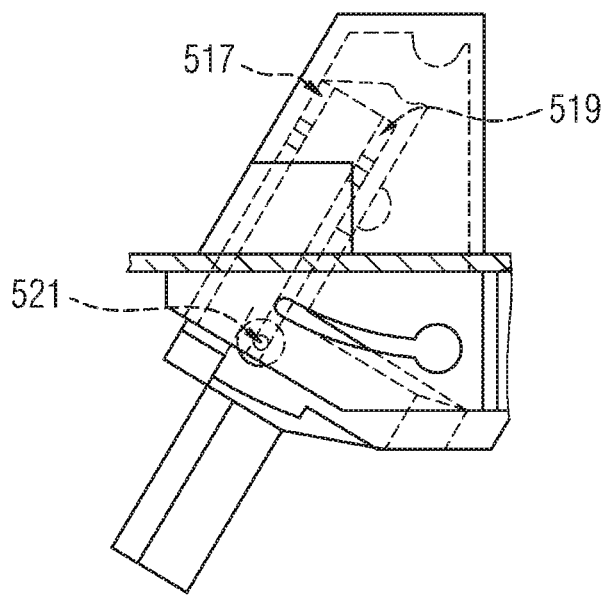
Figure 5F:
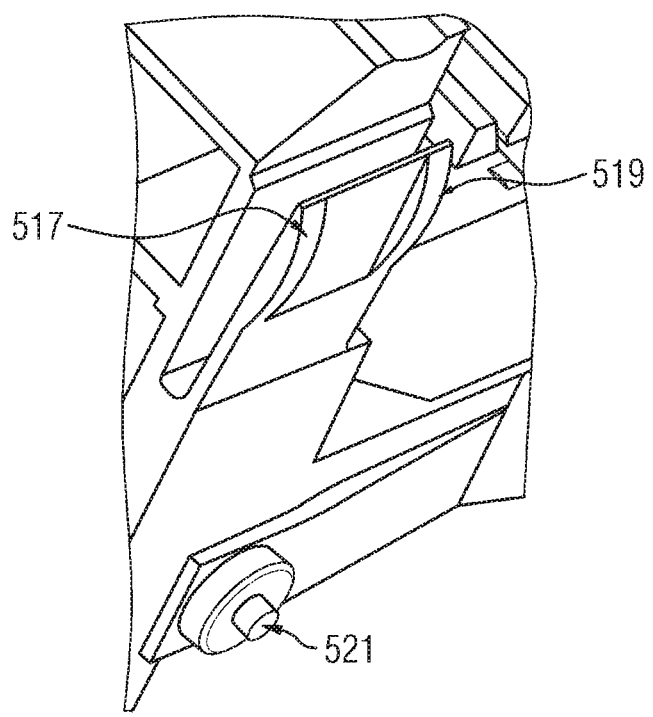

FIG. 5f shows a second position of the sound transducer unit during assembly of the second container system, in each case with two opposing parallel ribs 517, 519 on the vertical clips, and a respective opposing protrusion 521 formed as a guide pin on the horizontal clip.

Figure 5G:
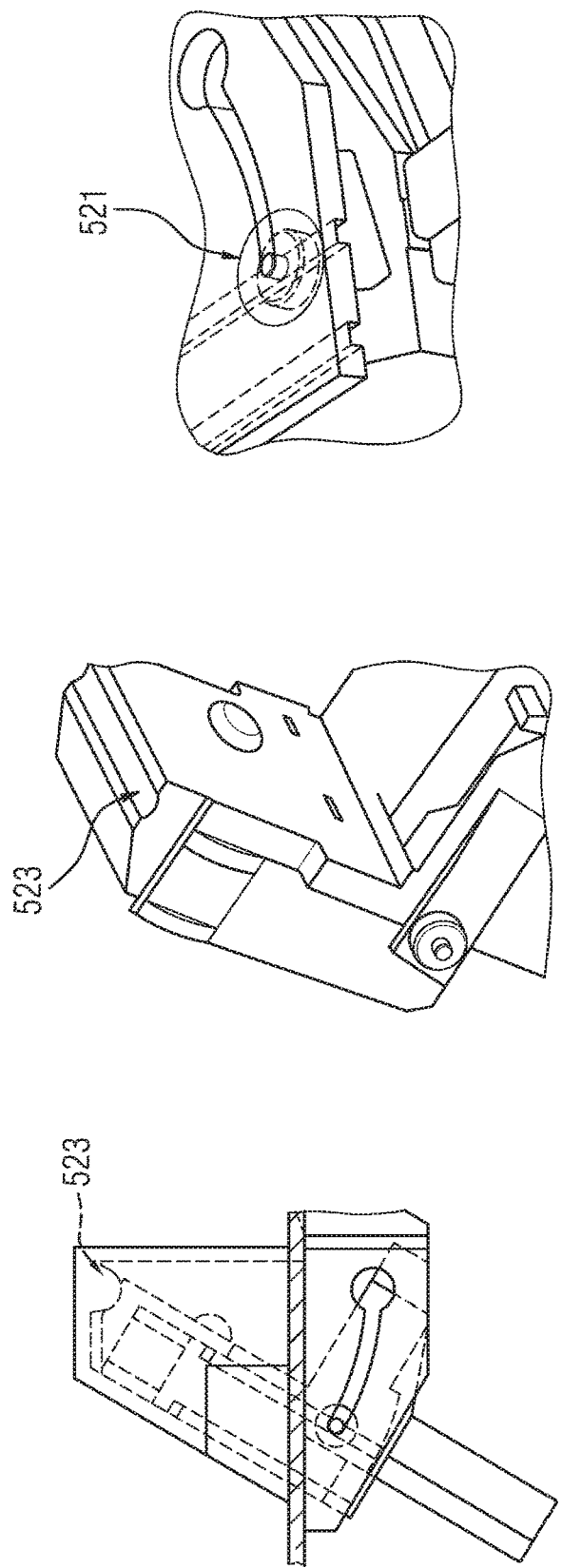

FIG. 5g shows a third position of the sound transducer unit during assembly of the container system, with a semi-cylindrical bearing 523. Guide elements 513, 515, 517, 519 are released so that the sound transducer unit is pivoted by means of the guide pin.

Figure 5H:
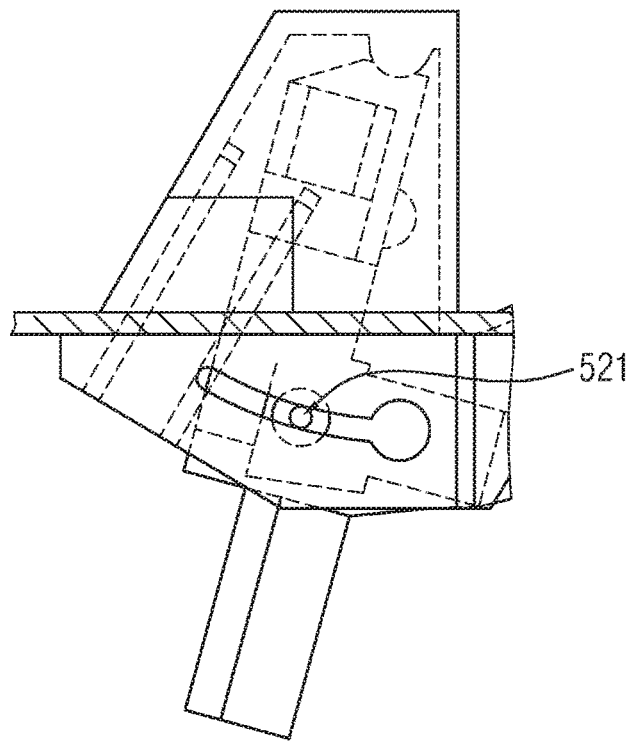
Figure 5H:
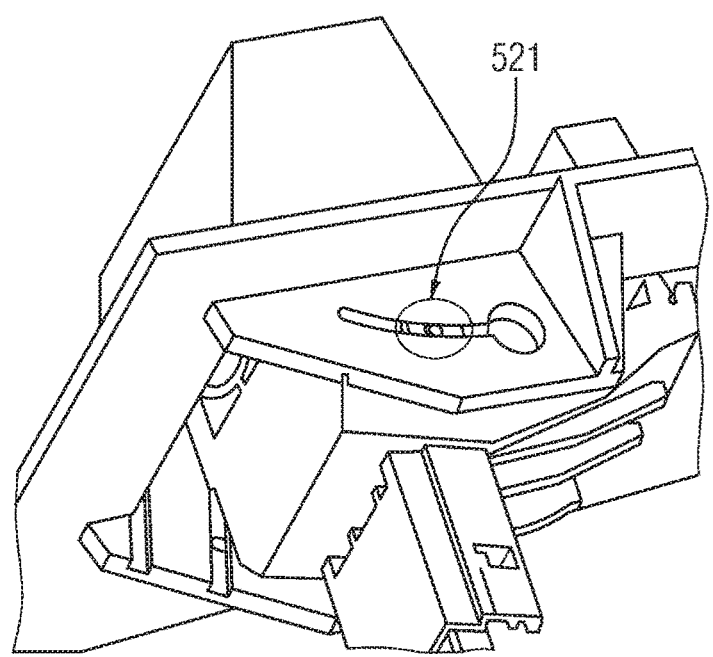

FIG. 5h shows a fourth position of the sound transducer unit during assembly of the second container system, in which the protrusion 521 formed as a guide pin on the horizontal clip is pivoted into a round gap.

Figure 5I:
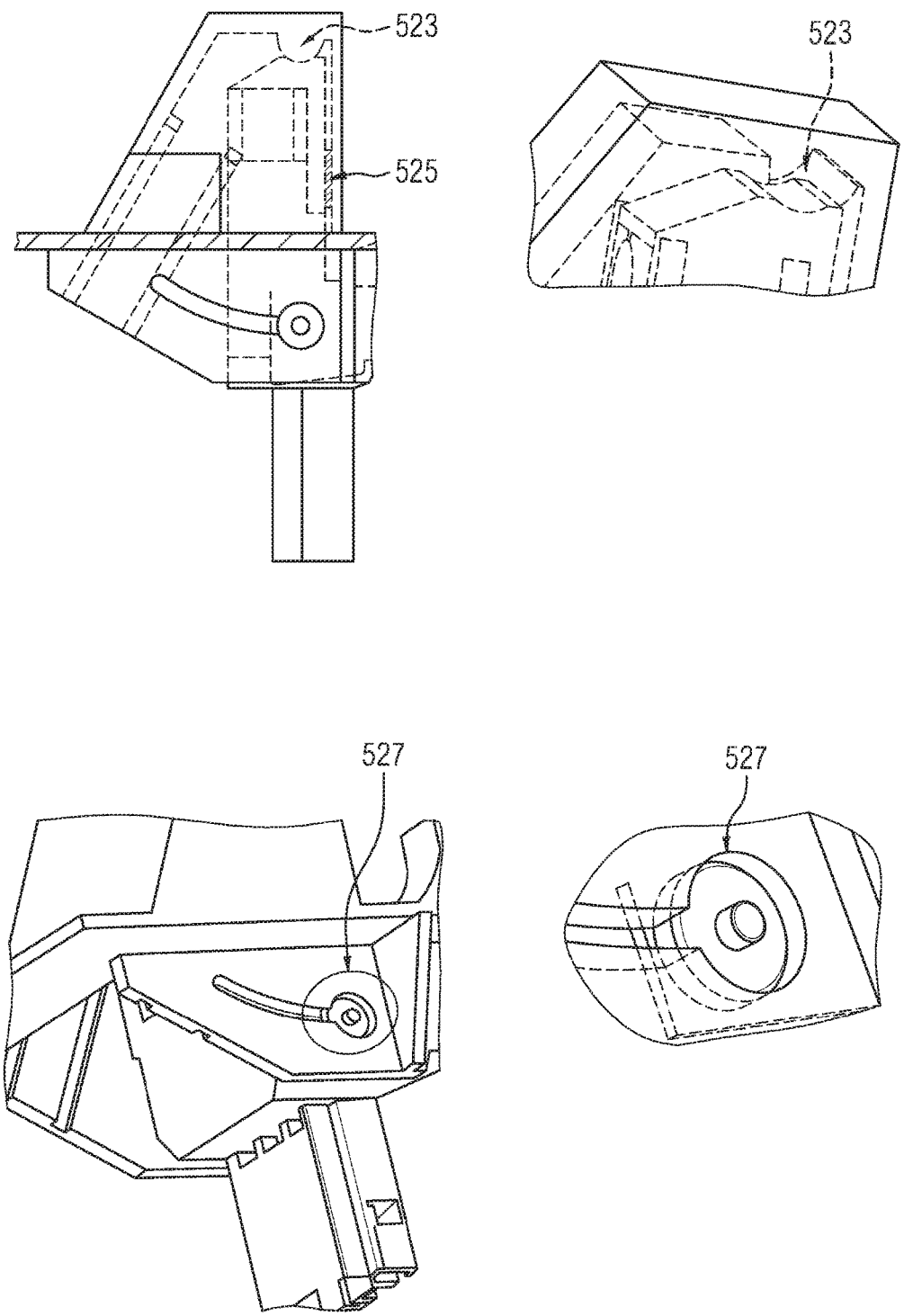

FIG. 5i shows a fifth position of the sound transducer unit during assembly of the second container system, in which the horizontal clips are engaged in and released from cylindrical holes 527, so that the end position of the sound transducer unit is guaranteed by means of the semicylindrical bearing 523. A coupling element 525 is pressed tightly into a predefined gap in the end position.

In other exemplary embodiments, a container system is configured such that a sound transducer unit is introduced vertically into a cavity of a container (not shown). For example, for this a sliding block guide is assigned to the sound transducer unit and the container. Alternatively, the sound transducer unit is introduced for example free from guidance by the sliding block guide.

On production of this container system, the sound transducer unit is introduced vertically into the container and for example moved horizontally into an end position relative to the container by means of a wedge and screw.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A container system for a fluid, comprising:
   a container for storing the fluid, the container having an outer wall and a cavity;
   a sound transducer unit for measuring the fluid;
   a longitudinal axis extending through the sound transducer unit;
   a sliding block guide for guiding the movement of the sound transducer unit relative to the container; and
   a coupling element for acoustically coupling the sound transducer unit with the container;
   wherein as the sound transducer unit is introduced into the cavity, a first movement travel of the sound transducer unit relative to the container occurs such that the coupling element is substantially free from contact from the sound transducer unit and the outer wall, and then a second movement travel occurs such that the sound transducer unit pivots relative to the container until the sound transducer unit reaches an end position in which the coupling element is pressed between the outer wall and the sound transducer unit.

2. The container system of claim 1, the sliding block guide further comprising:
   a slotted-guide element; and
   a sliding block moveable relative to the slotted-guide element;
   wherein the movement of the slotted-guide element relative to the sliding block guides the movement of the sound transducer unit relative to the container.

3. The container system of claim 2, wherein the slotted-guide element is formed as part of the sound transducer unit, and the sliding block is formed as part of the container.

4. The container system of claim 2, wherein the slotted-guide element is formed as part of the container, and the sliding block is formed as part of the sound transducer unit.

5. The container system of claim 2, further comprising a contour formed as part of the slotted guide element, wherein the contour guides the movement of the sound transducer unit relative to the container during the first movement travel.

6. The container system of claim 2 wherein the slotted-guide element and the sliding block are configured for fixing the sound transducer unit relative to the container once the sound transducer unit is in the end position.

7. The container system of claim 1, further comprising an articulation point for guiding the sound transducer unit relative to the container during the second movement travel.

8. The container system of claim 7, the articulation point further comprising:
a pivot head;
a pivot cup engaged with the pivot head;
wherein the movement of the pivot head relative to the pivot cup guide the sound transducer unit relative to the container during the second movement travel.

9. The container system of claim 8, wherein the pivot head is formed as part of the container, and the pivot cup is formed as part of the sound transducer unit.

10. The container system of claim 8, wherein the pivot head is formed as part of the sound transducer unit, and the pivot cup is formed as part of the container.

11. The container system of claim 1, further comprising at least one additional guide wall formed as part of the container, the at least one additional guide wall being part of the sliding block guide.

12. A method for producing a container system for a fluid, comprising the steps of:
providing a container for storing a fluid;
providing an outer wall formed as part of the container;
providing a cavity formed as part of the container, a portion of the outer wall forming part of the cavity;
providing a sound transducer unit for measuring the fluid;
providing a longitudinal axis extending though the sound transducer unit;
providing a coupling element connected to the outer wall;
acoustically coupling the sound transducer unit with the container using the coupling element;
providing a first movement travel; and
providing a second movement travel;
moving the sound transducer unit according to the first movement travel such that the sound transducer moves relative to the container such that the coupling element is substantially free from mechanical contact with either the sound transducer unit or the outer wall as the sound transducer unit is moved into the cavity;
moving the sound transducer according to the second movement travel such that the sound transducer is pivoted relative to the container until the sound transducer unit reaches an end position relative to the container in which the coupling element is pressed between the outer wall and the sound transducer unit.

13. The method of claim 12, further comprising the steps of:
providing a sliding block guide;
guiding the movement of the sound transducer unit relative to the container using the sliding block guide.

14. The method of claim 13, further comprising the steps of:
providing slotted-guide elements which are part of the sliding block guide; and
providing sliding blocks which are part of the sliding block guide;
coupling the slotted-guide elements with the sliding blocks to guide the movement of the sound transducer unit relative to the container.

15. The method of claim 14, further comprising the steps of:
forming the slotted-guide element as part of the sound transducer unit; and
forming the sliding block as part of the container;
using the slotted-guide element and the sliding block to guide the sound transducer unit relative to the container during the first movement travel and in the second movement travel.

16. The method of claim 14, further comprising the steps of:
forming the slotted-guide element is formed as part of the container; and
forming the sliding block as part of the sound transducer unit;
using the slotted-guide element and the sliding block to guide the sound transducer unit relative to the container during the first movement travel and in the second movement travel.

17. The method of claim 14, further comprising the steps of fixing the sound transducer unit using the slotted-guide element and the sliding block once the sound transducer unit reaches the end position relative to the container.

18. The method of claim 12, further comprising the steps of:
providing an articulation point;
guiding the sound transducer unit relative to the container during the second movement travel using the articulation point.

19. The method of claim 18, further comprising the steps of:
providing a pivot head, the pivot head being part of the articulation joint; and
providing a pivot cup engaged with the pivot head, the pivot cup being engaged with the articulation joint;
guiding the movement of the sound transducer unit relative to the container during the second movement travel using the relative movement between the pivot head and the pivot cup.

20. The method of claim 18, further comprising the steps of:
forming the pivot head as part of the container; and
forming the pivot cup as part of the sound transducer;
guiding the movement of the sound transducer unit relative to the container during the second movement travel using the pivot head and the pivot cup.

21. The method of claim 18, further comprising the steps of:
forming the pivot head as part of the sound transducer; and
forming the pivot cup as part of the container;
guiding the movement of the sound transducer unit relative to the container during the second movement travel using the pivot head and the pivot cup.

* * * * *